(12) United States Patent
Almirall et al.

(10) Patent No.: US 8,668,873 B2
(45) Date of Patent: Mar. 11, 2014

(54) METHOD AND APPARATUS FOR EXTRACTION, DETECTION, AND CHARACTERIZATION OF VAPORS FROM EXPLOSIVES, TAGGANTS IN EXPLOSIVES, CONTROLLED SUBSTANCES, AND BIOHAZARDS

(75) Inventors: Jose Almirall, Miami, FL (US); Jeannette Perr, Miami, FL (US); Patricia Guerra, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 426 days.

(21) Appl. No.: 12/135,954

(22) Filed: Jun. 9, 2008

(65) Prior Publication Data

US 2009/0084201 A1 Apr. 2, 2009

Related U.S. Application Data

(63) Continuation-in-part of application No. 11/630,559, filed as application No. PCT/US2006/004074 on Feb. 2, 2006.

(60) Provisional application No. 60/649,464, filed on Feb. 2, 2005.

(51) Int. Cl.
*G01N 33/22* (2006.01)

(52) U.S. Cl.
USPC ............................... 422/88; 422/83; 422/527

(58) Field of Classification Search
None
See application file for complete search history.

(56) References Cited

U.S. PATENT DOCUMENTS

| | | | |
|---|---|---|---|
| 5,083,019 A | 1/1992 | Spangler | |
| 6,656,738 B1 | 12/2003 | Vogel et al. | |
| 6,815,216 B2* | 11/2004 | Sandra et al. | 436/178 |
| 2001/0045000 A1* | 11/2001 | Gundel et al. | 29/458 |
| 2002/0098594 A1 | 7/2002 | Sandra et al. | |
| 2004/0248319 A1 | 12/2004 | Belyakov et al. | |

OTHER PUBLICATIONS

Yamamoto, Takatoki et al. "PDMS-glass hybrid microreactor array with embedded temperature control device. Application to cell-free protein synthesis." Lab on a Chip (2002) 2 p. 197-202.*

Lorenzo, Norma et al. "Laboratory and field experiments used to identify Canis lupus var. familiaris active odor signature chemicals from drugs, explosives, and humans." Analytical and Bioanalytical Chemistry (2003) 376 p. 1212-1224.*

(Continued)

*Primary Examiner* — Christopher A Hixson
(74) *Attorney, Agent, or Firm* — Marshall, Gerstein & Borun LLP

(57) ABSTRACT

An improved method of extraction, detection, and characterization of a vapor from an explosive, a taggant in an explosive, a controlled substance, a biohazard, and mixtures thereof uses a new and improved SPME device for extraction and ion mobility spectrometry for detection and characterization. The new and improved SPME device has an increased capacity to sorb a target vapor. The increased sorption of vapor provides for more accurate detection by an ion mobility spectrometer. A SPME device having increased surface area may be exposed to an atmosphere in an enclosure containing a test object or a volume of gas that was in contact with the test object to allow for sorption of the target vapor and then introduced into an IMS for more accurate detection and characterization of the vapor due to the increased sorption of the vapor by the SPME device described herein.

10 Claims, 4 Drawing Sheets

(56) References Cited

OTHER PUBLICATIONS

Buxton, Tricia L. et al. "Trace explosive detection in aqueous samples by solid-phase extraction ion mobility spectrometry (SPE-IMS)." Applied Spectroscopy (2003) 57 p. 223-232.*

Ferguson, Gregory S. et al. "Contact adhesion of thin gold films on elastomeric supports: cold welding under ambient conditions." Science (1991) 253 p. 776-778.*

Liu, Wenmin et al. "Preparation of stir bars for sorptive extraction using sol-gel technology." Journal of Chromatography A (2004) 1045 15-22.*

Bicchi, Carlo et al. "Headspace Sorptive Extraction (HSSE), Stir Bar Sorptive Extraction (SBSE), and Solid Phase Microextraction (SPME) Applied to the Analysis of Roasted Arabica Coffee and Coffee Brew." Journal of Agricutural and Food Chemistry (2002) 50 449-459.*

Almirall et al., "Field Recovery of Explosive Residues Using Solid-Phase Microextraction Followed by Chromatographic Analysis," *Proc. SPIE*, 35:18-23 (1999).

Borsdorf et al., "Corona Discharge Ion Mobility Spectrometry of Aliphatic and Aromatic Hydrocarbons," *Anal. Chim. Acta*, 403:235-242 (2000).

Dworzanski et al., "Field-Portable, Automated Pyrolysis-GC/IMS System for Rapid Biomarker Detection in Aerosols: A Feasibility Study," *Field Anal. Chem. Technol.*, 1(5):295-305 (1997).

Ewing et al., "Detection of Volatile Vapors Emitted from Explosives with a Handheld Ion Mobility Spectrometer," *Field. Anal. Chem. Technol.*, 5(5):215-221 (2001).

Franquet et al., "Study of the Effect of Different Aluminum Surface Pretreatments on the Deposition of Thin Non-Functional Silane Coatings," *Surf. Interface Anal.*, 36(8):681-684 (2004).

Furton et al., "Application of Solid-Phase Microextraction to the Recovery of Explosives and Ignitable Liquid Residues from Forensic Specimens," *J. Chromatogr. A*, 885(1-2):419-432 (2000).

Furton et al., "Optimization of Biological and Instrumental Detection of Explosives and Ignitable Liquid Residues Including Canines, SPME/ITMS and GC/MS$^{n}$," *Proc. SPIE—Int. Soc. Opt. Eng.*, 5071:183-192 (2003).

Furton et al., "Optimization of SPME for the Recovery of Explosives from Aqueous and Post-Explosion Debris Followed by Gas and Liquid Chromatographic Analysis," *J. Forensic Sci.*, 45:845-852 (2000).

Furton et al., The Scientific Foundation and Efficacy of the Use of Canines as Chemical Detectors for Explosives, *Talanta*, 54(3):487-500 (2001).

Furton et al., "The Use of Solid-Phase Microextraction-Gas Chromatography in Forensic Analysis," *J. Chromatogr. Sci.*, 38(7):297-306 (2000).

Hill et al., "Capabilities and Limitations of Ion Mobility Spectrometry for Field Screening Applications," *Field Anal. Chem. Technol.*, 1:119-134 (1997).

Kirkbride et al., "Application of Solid-Phase Microextraction to the Recovery of Organic Explosives," *J. Forensic Sci.*, 43(1):76-81 (1998).

Lai et al., "Analysis of Volatile Components of Drugs and Explosives by Solid Phase Microextraction-Ion Mobility Spectrometry," *J. Sep. Sci.*, 31(2):402-412 (2008).

Leonhardt, "New Detectors in Environmental Monitoring using Tritium Sources," *Radioanal. Nucl. Chem.*, 206(2):333-339 (1996).

Lesure et al., "Photoionization in Air with Ion Mobility Spectrometry Using a Hydrogen Discharge Lamp," *Anal. Chem.*, 58(11):2142-2147 (1986).

Lubman et al., "Plasma Chromatography with Laser-Producted Ions," *Anal. Chem.*, 54(9):1546-1551 (1982).

Matz et al., "Evaluation of Suspected Interferents for TNT Detection by Ion Mobility Spectrometry," *Talanta*, 54:171-179 (2001).

Miller et al., "A MEMS Radio-Frequency Ion Mobility Spectrometer for Chemical Vapor Detection," *Sens Actuators A*, 91:301-312 (2001).

Munro et al., "Characterisation of the Ion Mobility Spectrometric Behaviour of a Dinitrobutane Under Varying Conditions of Temperature and Concentration," *Anal. Chim. Acta.*, 375(1-2):49-63 (1998).

Nambayah et al., "A Quantitative Assessment of Chemical Techniques for Detecting Traces of Explosives at Counter-Terrorist Portals," *Talanta*, 63(2):461-467 (2004).

Valentine et al., "Multidimensional Separations of Complex Peptide Mixtures: A Combined High-Performance Liquid Chromatography/Ion Mobility/Time-of-Flight Mass Spectrometry Approach," *Int. J. Mass Spectrom.*, 212(1-3):97-109 (2001).

Williams et al., "Canine Detection Odor Signatures for Explosives," *Proc. SPIE*, 3575:291-301 (1998).

Yinon, *Forensic Applications of Mass Spectrometry*, CRC Press (1995). Table of Contents Only.

"Convention on the Marking of Plastic Explosives for the Purpose of Detection," Retrieved from the internet on Feb. 6, 2008: URL:http://www.mcgill.ca/files/iasl/montreal1991.pdf.

Cottingham, "Product Review: Ion Mobility Spectrometry Rediscovered," *Anal. Chem.*, 75:435A-439A (2003).

Ewing et al., "A Critical Review of Ion Mobility Spectrometrey for the Detection of Explosives and Explosive Related Compounds," *Talanta*, 54:515-529 (2001).

Handley et al., "Great Ideas of a Decade," *Anal. Chem.*, 73:660A-666A, (2001).

Moore, "Instrumentation for Trace Detection of High Explosives," *Rev. Sci. Instrum.*, 75:2499-2512 (2004).

Perr et al., "Solid Phase Microextraction Ion Mobility Spectrometer Interface for Explosive and Taggant Detection," *J. Sep. Sci.*, 28(2):177-183 (2005).

Yinon, "Handheld Chemical-Sensing Systems Come in Several Varieties and Offer Advantages over the Traditional Bomb-Sniffing Dog," *Anal. Chem.*, 75(5):98A-105A (2003).

International Search Report for Application No. PCT/US2006/004074, dated Dec. 10, 2007.

* cited by examiner

METHOD AND APPARATUS FOR EXTRACTION, DETECTION, AND CHARACTERIZATION OF VAPORS FROM EXPLOSIVES, TAGGANTS IN EXPLOSIVES, CONTROLLED SUBSTANCES, AND BIOHAZARDS

CROSS-REFERENCE TO RELATED APPLICATIONS

This is a continuation-in-part of U.S. application Ser. No. 11/630,559 filed Dec. 21, 2006, which is a U.S. National Stage of PCT/US2006/004074, filed Feb. 2, 2006, based on U.S. Provisional Application 60/649,464, filed Feb. 2, 2005.

STATEMENT OF GOVERNMENTAL INTEREST

This invention was made with government support under grant 2006-DN-BX-K027 awarded by the National Institute of Justice. The government has certain rights in the invention.

BACKGROUND

Ion mobility spectrometry (IMS) is a rugged, inexpensive, sensitive, field portable technique for the detection of organic compounds. It is widely employed in ports of entry and by the military as a particle detector for explosives and drugs of abuse. Many organic high explosives do not have a high enough vapor pressure for effective vapor sampling. However, these explosives and their commercial explosive mixtures have characteristic volatile components detectable in a headspace when contained. In addition, taggants are added to commercially-manufactured explosives to aid in detection through headspace sampling. Solid phase microextraction (SPME) is an effective extraction technique that has been successfully employed in the field for the absorption and/or adsorption of a variety of compounds. SPME can easily extract these compounds from the headspace for IMS vapor detection.

In 1996, Congress passed the Anti Terrorism Bill, which requires the addition of detection taggants to plastic explosive compounds and the ban of sale or import of plastic explosives that do not contain a detection agent [Public Law 104-132, Antiterrorism and Effective Death Penalty Act of 1996; Section 603; Apr. 24, 1996]. A detection taggant is a solid or liquid vapor emitting substance added to an explosive material to facilitate discovery before detonation. A detection taggant can easily be detected by explosive vapor detectors, such as ion mobility spectrometers (IMS). IMS are currently used as particle detectors requiring the manual transfer of particles from a suspect area and thermal desorption into the spectrometer.

Many organic high explosives, particularly those found in plastic explosives, do not produce a significant vapor pressure to allow headspace vapor detection, especially in the field [R. G. Ewing, C. J. Miller, Field Anal. Chem. Technol., 5:215-221 (2001)]. The International Civil Aviation Organization (ICAO) has designated the detection taggant compounds as the following four compounds in the indicated concentrations by mass: 0.5% 2-nitrotoluene (2-NT), 0.5% 4-nitrotoluene (4-NT), 0.1% 2,3-dimethyl-2,3-dinitrobutane (DMNB), and 0.2% ethylene glycol dinitro (EGDN) [Convention on the Marking of Plastic Explosives for the Purpose of Detection, http://www.mcgill.ca/files/ias1/montreal1991.pdf, accessed Feb. 6, 2008]. These compounds were selected because they are not commonly found in nature, they do not hinder the explosive properties of the tagged compound, they continue to release their vapors at a steady rate for 5 to 10 years, they do not present a significant environmental hazard, and they do not readily adhere to common substances the taggant may come in contact with [J. Yinon, Forensic Applications of Mass Spectrometry, CRC Press, Boca Raton, Fla., 1995]. In addition to taggant detection to determine if an improvised explosive device is present, there are also additional odor signature compounds present in significant amounts for detection [M. Williams, J. M. Johnston, M. Cicoria, E. Paletz, L. P. Waggoner, C. Edge, S. F. Hallowell, Proc. SPIE, 35:291-301 (1998)]. These odor signature compounds can be extracted using SPME and detected by IMS [J. M. Perr, K. G. Furton, J. R. Almirall, J. Sep. Sci., 28:177-183 (2005). 2. H. Lai, P. Guerra, M. Joshi, J. R. Almirall, J. Sep. Sci., 31: 402-412 (2008)].

The Transportation Security Administration (TSA) has mandated that all airports in the United States screen all bags for explosives [http://www.aviationnow.com/avnow/news/channel_comm.jsp?view=story & id=news/captl130.xml, accessed Mar. 12, 2003]. IMS is one of the screening tools approved by the TSA. These instruments can detect the taggants selected by the ICAO [R. G. Ewing, D. A. Atkinson, G. A. Eiceman, G. J. Ewing, Talanta, 54:515-529 (2001)]. Detector dog teams are another widely used screening tool [D. S. Moore, Rev. Sci. Instrum., 75:2499-2512 (2004)].

IMS is a presumptive detection method for organic compounds that is extremely fast, straightforward to use, low cost, with clear-cut data interpretation, excellent sensitivity, and low power demands. Run times for commercial IMS range from 1 to 7 seconds. IMS machines have a large installed base of over 10,000 commercial instruments and 50,000 military instruments conducting over 10,000,000 analyses per year [K. Cottingham, Anal. Chem., 75:435A-439A (2003)]. The false positive rate for swabbing of suspected areas is reported to be less than 1% while the false positive rate for air sampling of suspected areas is less than 0.1% [Itemiser Contraband (Drug and Explosive) Detection and Identification System User's Manual revision 3.1., GE Ion Track Instruments, Wilmington, Mass. (1999)]. For example, when seventeen of the most likely false positives for 2,4,6-trinitrotoluene (2,4,6-TNT) were studied, it was found that only seven of those were detected by the IMS and upon careful analysis, the compound that displayed the most similar mobility to TNT, 4,6-dinitro-o-cresol (4,6-DN-o-C), did not produce a false positive [L. M. Matz, P. S. Tornatore, H. H. Hill, Talanta, 54:171-179 (2001)]. IMS has also been evaluated as a field screening application and found to have a number of advantages over other field deployable techniques [H. H. Hill, G. Simpson, Field Anal. Chem. Technol., 1:119-134 (1997)].

In IMS, ions are separated and recognized on the basis of their mobility values. Some instruments can analyze only positive or negative ions in a determination, while other instruments can analyze both positive and negative ions in the same analytical determination. The detection of explosives and taggants are typically conducted in the negative ion mode. Mobility (K in $cm^2/V$ s) is determined using the drift velocity (vd in cm/s) of the ion through a heated drift tube and a weak electric field (E in V/cm) that the ion is exposed to when inside the heated drift tube (vd=E×K). Ionization occurs in the reaction region when a 63Ni source initiates ionization by emitting β particles. The β particles trigger a cascade of ionization reactions, either with the air or with a dopant gas present in the ionization region, to produce reactant ions. The reactant ions interact with the sample through ion molecule interactions to generate product ions that are detected during the analysis. Other ionization methods can be used, such as a tritium β particle emitter [J. W. Leonhardt, J.

Radioanal. Nucl. Chem., 206:333 (1996)], photoionization [D. D. Lubman, M. N. Kronick, Anal. Chem., 54:1546 (1982); C. S. Lesure, M. E. Fleischer, G. K. Anderson, G. A. Eiceman, Anal. Chem., 58:2142 (1996); H. Borsdorf, H. Schelhorn, J. Flachowsky, H. Döring, J. Stach, Anal. Chim. Acta., 403:235-242 (2000)], and corona discharge [R. A. Miller, E. G. Nazarov, G. A. Eiceman, T. A. King, Sens. Actuators A, 91:301-312 (2001)], but ionization using the 63Ni source is the most common. Ionization results in either molecular ion or molecular clusters related to the molecular ion. Fragmentation is a rare occurrence but it has been observed in very special cases [K. Cottingham, Anal. Chem., 75:452A (2003)].

Also during IMS, an electronic gate opens at timed intervals throughout the run to allow the ions to enter the drift region for separation to occur. The opening of the electronic gate begins the timing of the ion's flight time to reach the detector in order to calculate the drift velocity. A linear potential drop exists in the drift region to move the reactant and product ions towards the detector. Neutrals and ions of the opposite charge being analyzed are swept out of the drift region by a counter-current flow of drift gas. A plasmagram results as a plot of the current measured at the collector electrode with respect to time in the millisecond (ms) time frame. The General Electric Ion Track Itemiser® 2 collects one plasmagram every 100 ms. For a 7 s run, 70 plasmagrams are recorded. The 70 collected plasmagrams then undergo a data deconvolution step in which a representative plasmagram is produced. An intensity map views all the plasmagrams collected during one run stacked on each other showing height as intensity. Dark areas represent peaks while lighter areas represent troughs. A single plasmagram can be imported into Excel and graphed.

An important factor that affects mobility is the collisional cross-sectional area ($\Omega d$ in Å2). The mean free path of an ion with a large collisional cross-section is shorter than those of a smaller collisional cross-section. If two molecules have the same collisional cross-section, the heavier molecule will have a longer mean free path due to its slower velocity. The dopant gas and air within the drift tube affect the drift velocity (vd) by collisions, making IMS a quasi mass analyzer but instead of using only mass to charge (m/z) it uses three different parameters: shape (collisional cross-section), mass, and charge.

SPME is a highly effective sample extraction technique that has been shown to be an effective tool for the analysis of volatile and semi-volatile components and was named one of the six great ideas in analytical chemistry of the last decade [K. G. Furton, J. Wang, Y. L. Hsu, J. Walton, J. R. Almirall, J. Chromatogr. Sci., 38:297-306 (2000); K. G. Furton, J. R. Almirall, M. Bi, J. Wang, W. Lu, J. Chromatogr. A, 885:419-432 (2000); K. P. Kirkbride, G. Klass, P. E. Pigou, J. Forensic Sci., 43:76-81 (1998); J. Handley, C. M. Harris, Anal. Chem., 73:23A-26A (2001)]. Volatile or semi-volatile compounds are extracted by absorption and/or adsorption onto a nonvolatile polymeric coating or solid sorbent phase. After the analytes are sorbed onto the SPME phase they are commonly volatilized by thermal desportion in an injection port. SPME devices come in a variety of forms including but not limited to: articles coated in the SPME phase, vessels lined with the SPME phase, and SPME coated stir bars. A common and commercially available form of SPME is a fiber configuration. SPME has been successfully applied to the recovery of explosives and explosive vapors followed by GC/MS and HPLC analysis [J. R. Almirall, L. Wu, M. Bi, M. W. Shannon, K. G. Furton, Proc. SPIE, 35:18-23 (1999); K. G. Furton, L. Wu, J. R. Almirall, J. Forensic Sci., 45:845-852 (2000); K. G. Furton, R. J. Harper, J. M. Perr, J. R. Almirall, Proc. SPIE, 5071:183-192 (2003)]. Polydimethyl siloxane (PDMS) fibers have been reported as the most effective and rugged fiber for rapid headspace extraction of explosives with the least amount of carry-over problems [N. Lorenzo, T. Wan, R. J. Harper, Y. Hsu, M. Chow, S. Rose, K. G. Furton, J. Anal. Bioanal. Chem., 376:1212-1224 (2003)] for explosive compounds.

SPME is a very effective tool for the extraction of taggants from headspace samples under ambient environmental conditions that can also be used for remote sampling. Ion mobility spectrometry is a very effective tool for detecting trace amounts of explosives and explosive taggants under ambient environmental conditions [M. Nambayah, T. I. Quickenden, Talanta, 63:461-467 (2004)]. Ion mobility spectrometers have been successfully interfaced to other sample introduction techniques such as a solid phase extraction (SPE) [T. L. Buxton, P. B. Harrington, Appl. Spectrosc., 57:223-232 (2003)], gas chromatography (GC) [J. P. Dworzanski, W. H. McClennen, P. A. Cole, S. N. Thornton, H. L. C. Meuzelaar, N. S. Arnold, A. P. Snyder, Field Anal. Chem. Technol., 1:295-305 (1997)], and liquid chromatography (LC) [S. J. Valentine, M. Kulchania, C. A. S. Barnes, D. E. Clemmer, Int. J. Mass Spectrom., 212:97-109 (2001)].

A SPME-IMS interface has been created to couple the extraction efficiency of SPME to the detection capability of IMS. The demand for this sort of field portable, remote, reliable sampling is high [J. Yinon, Anal. Chem., 75:99A-105A (2003)]. The SPME-ISM interface shown meets this need by extracting vapors from explosives, taggants in explosives, controlled substances, biohazards, and mixtures thereof (detectable target vapors or detectable vapors) from a headspace for subsequent detection by a commercially available IMS in a simple, rapid, sensitive, and inexpensive manner.

Ranges may be expressed herein as from "about" or "approximately" one particular value and/or to "about" or "approximately" another particular value. When such range is expressed, another embodiment includes from the one particular value and/or to the other particular value. Similarly, when values are expressed as approximates, by use of the antecedent "about" it will be under that the particular value forms another embodiment.

SUMMARY OF THE DISCLOSURE

An apparatus and method for extraction of a detectable target vapor from a volatile compound such as an explosive, taggant in an explosive, controlled substance, biohazard, and mixtures thereof and methods for subsequent detection and characterization of the target vapor by an ion mobility spectrometry (IMS) are disclosed. The apparatus may comprise a tube having an inlet; a resistor for heating the tube; a connector fitted to the inlet; a septum fitted and sealed to the connector; and a new and improved solid phase microextraction (SPME) device adapted to be first exposed to an atmosphere that has been exposed to an object that may contain a volatile compound such as an explosive, a taggant in an explosive, a controlled substance, a biohazard, or mixtures thereof, thereby allowing the SPME device to absorb and/or adsorb a detectable target vapor from the volatile compound. The SPME device may have increased surface area to allow for increased absorption and/or adsorption of the vapor. The SPME device may be further adapted to be introduced into the apparatus for volatilization and introduction of the vapor into a sample receiving area of an IMS for detection and characterization of the target vapor.

Also disclosed is a method for extraction, detection, and characterization of a vapor a volatile compound such as an explosive, a taggant in an explosive, a controlled substances, a biohazard, or mixtures thereof. The method may comprise the steps of: (1) exposing a SPME device to an atmosphere in an enclosure containing a test object, thereby allowing the SPME device to absorb and/or adsorb the target vapor emitted from said object thereby concentrating the target vapor in and/or on the SPME device; and (2) introducing the SPME device into a sample receiving area of an apparatus for volatilization of the concentrated target vapor from the SPME device and introduction of the concentrated target vapor into an IMS for detection and characterization of the vapor.

Another method for extraction, detection, and characterization of a vapor from a volatile compound such as an explosive, a taggant in an explosive, a controlled substance, a biohazard, or mixtures thereof may include the steps of: (1) contacting a test object with a volume of gas to form a mixture of said gas with a detectable vapor; (2) exposing a SPME device to said gas to allow for absorption and/or adsorption of the detectable target vapor; and (3) introducing the SPME device into an apparatus for thermal desorption and introduction of the target vapor into an IMS for detection and characterization of the target vapor.

The SPME device described herein has increased surface area adapted for improved absorption and/or adsorption of a vapor from a volatile compound such as an explosive, a taggant in an explosive, a controlled substance, a biohazard, or mixtures thereof and subsequent, more reliable detection and characterization by an IMS. In accordance with the SPME devices and detection methods used and described here, the SPME devices may include a substrate and a volatile compound sorptive coating disposed on the substrate and capable of absorbing and/or adsorbing a vapor from an explosive, a taggant in an explosive, a controlled substance, a biohazard, or mixtures thereof in an amount sufficient for detection in an IMS. In accordance with a preferred embodiment, the SPME device may have a surface area of at least 50 mm$^2$.

A method of preparing the SPME devices having increased surface area is also disclosed. In one embodiment of the SPME devices and detection methods described herein, the SPME devices are prepared for accurate detection by first cleansing the substrate, e.g., with a cleansing agent or mixture, prior to coating the substrate; preparing a volatile compound sorptive coating mixture; and then coating the substrate with the volatile compound sorptive coating mixture to form a volatile compound sorptive coating that is capable of absorbing and/or adsorbing a target vapor from a volatile compound such as an explosive, a taggant in an explosive, a controlled substance, a biohazard, or mixtures thereof in an amount sufficient for detection in an IMS.

A new and improved method of extracting a detectable target vapor from a volatile compound such as an explosive, a taggant in an explosive, a controlled substance, a biohazard, or mixtures thereof using a new and improved SPME device having an increased capacity to sorb the target vapor is also disclosed. The improved absorption and/or adsorption of the vapor allows for better extraction of the target vapor and provides for more accurate detection and characterization by an IMS. In one embodiment of the new and improved method, the method may include preparing a new and improved SPME device, having increased surface area, and exposing the SPME device to an atmosphere in an enclosure containing a test object or a volume of gas that was in contact with the test object to allow for absorption and/or adsorption of the target vapor. The SPME device may then be introduced into a sample receiving area of an IMS for more accurate detection and characterization of the target vapor due to the increased absorption and/or adsorption of the target vapor by the SPME devices described herein.

The devices, apparatus, and methods described herein, together with further objects and attendant advantages, will be best understood by reference to the following detailed description, taken in conjunction with the accompanying drawings.

DETAILED DESCRIPTION OF DRAWINGS

Figure 1:
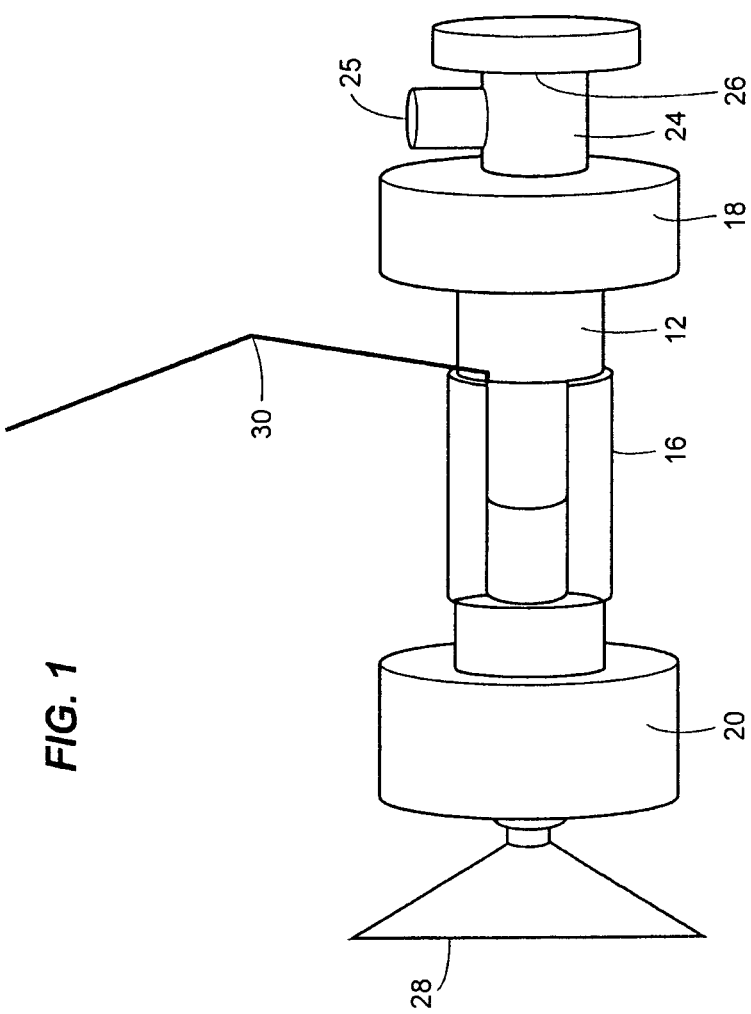
FIG. 1 is a first schematic representation of the SPME-IMS interface.
Figure 2:
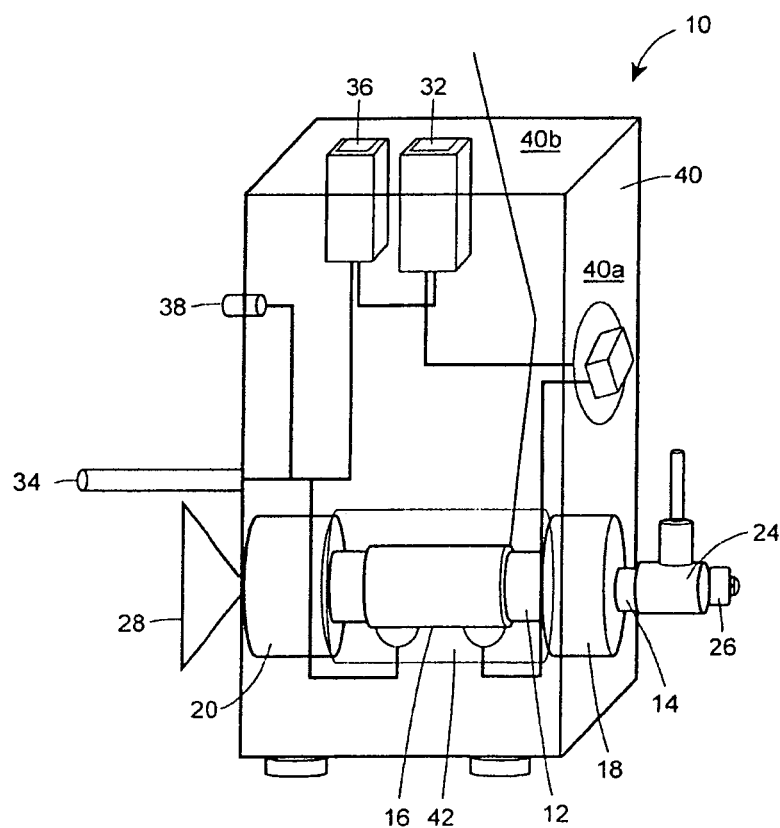
FIG. 2 is a second schematic representation of the SPME-IMS interface, which also includes an interface housing and related components.

Referring now to FIG. 1, a solid phase microextraction ion mobility spectrometry (SPME-INS) interface 10 is shown. The SPME-IMS interface 10 is a second generation prototype that was constructed for less than $1000 (US). An aluminum tube 12 was machined to form an inlet 14 (see FIG. 2) that can be heated using a resistor 16. A pentiostat 22 (see FIG. 2) was used to provide current to the resistor 16, for example. A first aluminum cylindrical heating block 18 and a second aluminum heating block 20 may also be disposed on or near opposite ends of the aluminum tube 12, as shown in FIGS. 1 and 2. The inlet 14 was coated with a +1200 Å (Silcosteel®) layer treatment (Restek, Bellefonte, Pa.) to deactivate the surface. Ultra high purity helium carrier gas (Air Products, Allentown, Pa.), the heat generated by the resistor 16, and the first and second cylindrical heating blocks 18, 20 were used to desorb the analytes off a SPME device 106. A calibrated 150 mm aluminum 15-turn high-accuracy valve flow meter from Gilmont® Instruments (Barrington, Ill.) was used to control the flow of helium through the SPME-IMS interface 10. Of course, various other types of valve flow meters may be used in conjunction with the interface 10 of the present invention, as this particular model is representative only. A Swagelok union "t" connector 24, purchased from Florida Fluid Systems Technologies, Inc. (Sunrise, Fla.) was fitted onto the sample thermal desorption inlet 14 (see FIG. 3). For example, a Swagelock Male Run Tee, ⅛ in. Tube OD×⅛ in. Male NPT×⅛ in. Tube OD may be used. A 5 mm Thermogreen septum 26 was machine punched out from an 11 mm Thermogreen Supelco (Bellefonte, Pa.) septa using a punch. The 5 mm septum 26 was fitted into one of the caps on the union "t" connector 24 and sealed in place using the back ferrule of the union "t" connector. Again, of course, other types of septa and connectors may be used in accordance with the interface 10 of the present invention, as the aforementioned components, while used in the SPME-IMS interface 10 described herein, are representative only. The total length of the SPME-IMS device is 11 cm.

Referring now to FIG. 2, the SPME-IMS interface 10 further includes a housing 40. The housing 40 may be formed of metal, a metal alloy, or other material. A thermocouple 30 is also shown (see also FIG. 1), which senses the temperature of the resistor 16 based on the principle that voltage is produced when two dissimilar metals are joined. The pentiostat 22 may be disposed on a first side 40a of the housing 40, as shown in FIG. 2, for example. A fuse 32 and a power switch 36 are disposed on a second side 40b of the housing 40, and a power cord 34 is disposed on a third side 40c of the interface housing 40. Of course, the pentiostat 22, the fuse 32, the power switch 36, and the power cord 34 may alternatively be disposed on other areas of the housing 40, resulting in alternative configurations that would not depart in the least from the spirit and scope of the present invention. An ion mobility spectrometer inlet nozzle 28, which is attached to interface 10 near the second aluminum cylindrical heating block 20, is also disposed on the third side 40c of the housing 40. Lastly, an insulating material 42, such as a glass wool insulating material, encircles the resistor 16.

Figure 3:
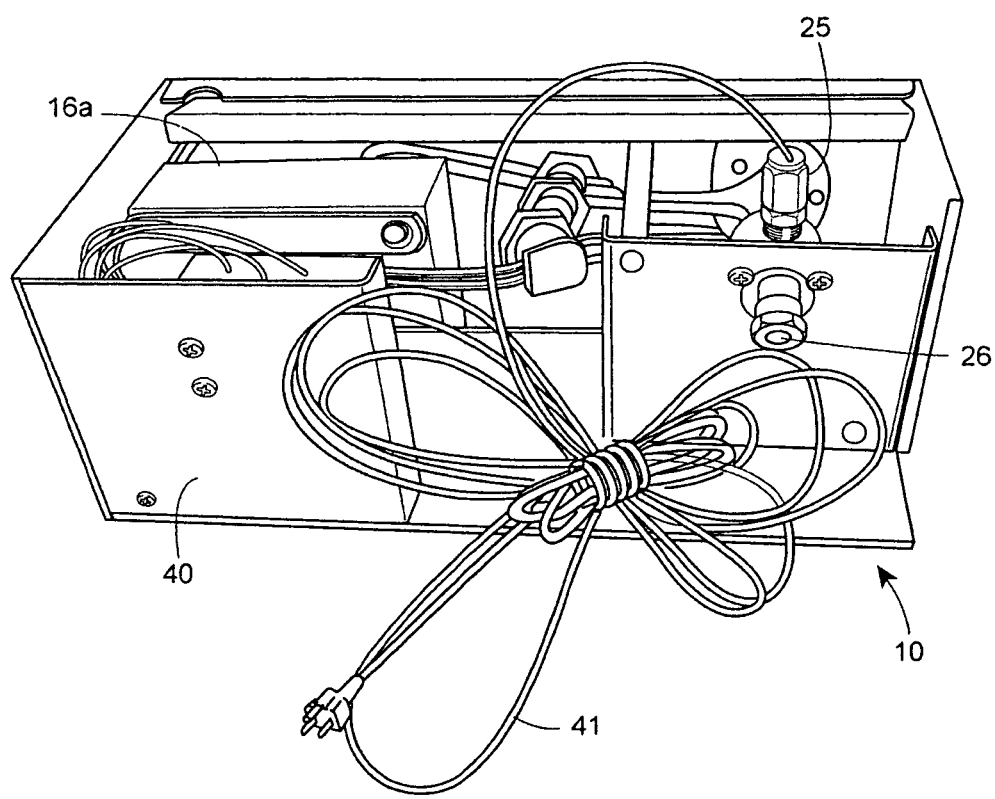
FIG. 3 is a front perspective view of an SPME-IMS interface in accordance with the present disclosure.

FIGS. 2-3 show a preferred embodiment of an SPME-IMS interface 10 in accordance with the present invention. Interface 10 has an outer housing 40 for mounting the various components of the interface 10. Flexible tubing 41 conveys a carrier gas from a source (not shown) to carrier gas inlet 25. Helium is a preferred carrier, but any other non-reactive gases could also be used.

A septum 26 is adapted to receive a SPME device 106 (not shown). Upon exposure to heat, vapors emitted from the SPME device 106 are conveyed by the carrier gas through connector 24. Referring to FIG. 3, heat may be supplied by a resistor 16 in the form of resistor block 16a, for example.

In accordance with the apparatus and methods described herein, a SPME device 106 having increased capacity for absorption and/or adsorption of a detectable target vapor is first exposed to air or other gaseous atmosphere in an enclosed space containing an object, e.g., a suitcase or other container having a volume sufficient to contain an explosive, biohazard, or controlled substance, allowing for sorption (i.e. absorption and/or adsorption) of the target vapor. The SPME device 106 is then introduced into the interface 10 for volatilization and introduction of the concentrated target vapor into the IMS. Volatilization of a detectable quantity of the target vapor can be achieved by thermal desorption. The IMS then detects and characterizes the target vapor to indicate whether a volatile compound such as an explosive, a taggant in an explosive, a controlled substance, a biohazard, or mixtures thereof are present in the object. Using the SPME device 106 and methods herein described, more accurate detection can be achieved.

A SPME device's 106 capacity for absorption and/or adsorption of a detectable target vapor as well as its sensitivity may be enhanced by increasing the amount of SPME-phase able to participate in the absorption and/or adsorption of the target vapor. By increasing the surface area of the SPME device 106, the amount of SPME-phase able to participate in absorption and/or adsorption of the vapor is increased without appreciably increasing sorption time. The SPME device 106 may also be sized for use in a sample receiving area 112 of a conventional IMS 110, thereby providing for a low cost method of performing SPME and IMS in combination.

Figure 4:
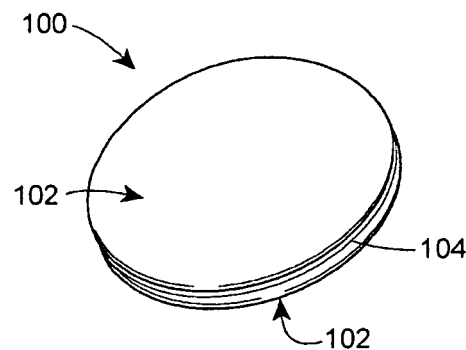
FIG. 4 is a perspective view of a substrate of a SPME device in accordance with the present disclosure.

Referring to FIG. 4, the SPME device 106 comprises a substrate 100 and a volatile compound sorptive coating 108. The substrate 100 may be, for example, substantially planar, and may have the shape of a rectangle, a square, or any other suitable geometry. Preferably, the substrate 100 has a disc shape. The substrate 100 may be formed of any suitable material such as, for example, a metal, plastic, or ceramic. For example, the substrate 100 may be glass, fused silica, aluminum, or stainless steel. The substrate 100 may be flexible or rigid. Preferably, the substrate 100 has a size and shape that substantially corresponds to the desired size and shape of the SPME device 106. Preferably, the SPME device 106 has a flat disc shape.

The substrate 100 has first and second major surfaces 102. The first and second major surfaces 102 may, for example, be planar. Preferably, the first and second major surfaces 102 have a circular shape. However, the first and second major surfaces 102 may have any other suitable shape, such as for example, a square or rectangular shape. The first and second major surfaces 102 may each have a surface area of from approximately 5 to 2500 mm². Preferably, the first and second major surfaces 102 each have a surface area of from approximately 60 to 100 mm². Most preferably, the first and second major surfaces 102 each have a surface area of from approximately 250 to 500 mm².

The substrate 100 may have one or more side surfaces 104 disposed between and integrally connected to the first and second major surfaces 102. The side surfaces 104 may be, for example, planar or rounded. The SPME device 106 may have a thickness of approximately 0.5 to 5 mm. Preferably, the SPME device 106 may have a thickness of approximately 0.5 to 2 mm.

Figure 5:
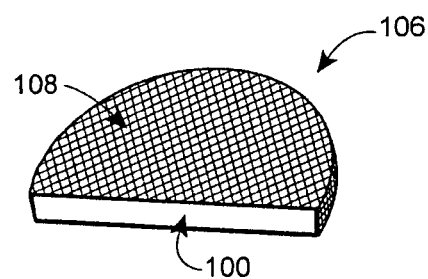
FIG. 5 is a cut-away view of a SPME device in accordance with the present disclosure.

Referring to FIG. 5, any one or more of the surfaces of the SPME device 106 can be coated with a vapor sorption medium, such as poly(dimethylsiloxane) to form a volatile compound sorptive coating 108. For example, an entire surface of the substrate 100, including the first and second major surfaces 102 and the one or more sides surfaces 104 may be coated with the vapor sorption medium such that the volatile compound sorptive coating 108 is disposed over the entire surface of the substrate 100. Alternatively, for example, only the first and second major surfaces 102 may be coated with the vapor sorption medium.

The volatile compound sorptive coating 108, is capable of absorption and/or adsorption of target vapors, such as vapors from explosives, taggants in explosives, controlled substances, biohazards, or mixtures thereof. The volatile compound sorptive coating 108 may have a thickness of approximately 20 to 200 μm.

Sorption media capable of sorbing (absorbing or adsorbing) a detectable quantity of target vapors include, for example, carbowax, carboxan, divinylbenzene, poly(dimethylsiloxane) (PDMS), sol-gel PDMS, carbowax/polyethylene glycol (CW/PEG), carbowax/templated resin (CW/TPR), carboxen/polydimethylsiloxane (CAR/PDMS), divinylbenzene/carboxen/polydimethylsiloxane (DVB/CAR/PDMS), polydimethylsiloxane/divinylbenzene (PDMS/DVB), and polyacrylate (PA), and the like. The preferred sorption medium is an absorbent siloxane coating, particularly PDMS and sol-gel PDMS. Any sorption media capable of forming a volatile compound sorptive coating 108 that is capable of absorbing and/or adsorbing target vapors may be used.

The SPME device 106 may have a total surface area, for example, of at least 25 mm². Preferably, the SPME device 106 may have a surface area of from approximately 25 to 5000 mm².

The surface area of the volatile compound sorptive coating 108 of the SPME device 106 is at least 25 mm². Preferably, the volatile compound sorptive coating 108 has a surface area of from approximately 25 to 5000 mm². More preferably, the volatile compound sorptive coating has a surface area of approximately 500 to 1000 mm².

Figure 6:
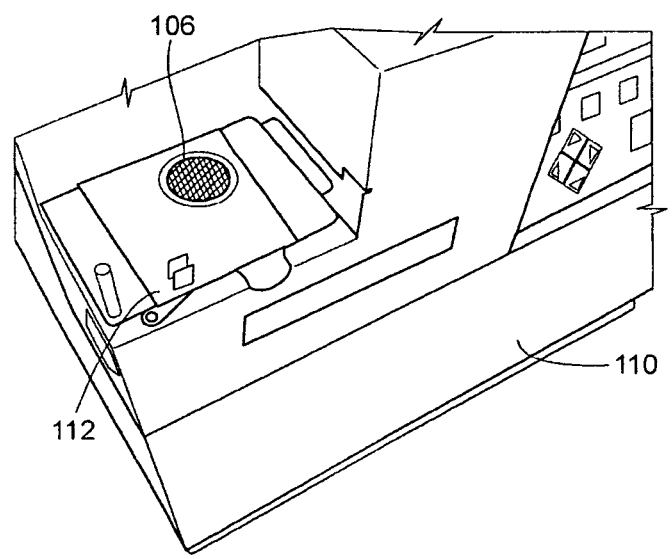
FIG. 6 is a perspective view of the SPME device of FIG. 5 disposed in the sample receiving area of an IMS.

Referring to FIG. 6, the SPME device 106 may be sized, for example, to substantially fit in a sample receiving area 112 of a conventional IMS 110. By sizing the SPME device 106 to fit in the sample receiving area 112 of a conventional IMS 110, SPME-IMS can be performed in combination without modification of the IMS 110 and, thus, at lower cost. Additionally, the SPME-IMS interface 10 may, for example, be adapted for loading of a SPME device 106. The SPME-IMS interface 10 may, for example, be adapted for loading of a SPME device 106 having a size and a shape that does not fit in the sample receiving area 112 of a conventional IMS 110; for example, a SPME device 106 that is larger than the sample receiving area 112 of a conventional IMS 110.

To form the SPME device 106, the substrate 100 having a desired size and geometry is prepared. The first and second major surface 102 and side surfaces 104 of the substrate 100 may be prepared, for example, by exposing the substrate 100 to a cleansing agent or mixture. The cleansing mixture may, for example, be a solution of $H_2SO_4$ and $H_2O_2$. The solution may consist, for example, of an approximately 2 to 1 ratio of $H_2SO_4$ to $H_2O_2$. The substrate 100 may then be rinsed using deionized water. If, for example, a glass substrate is used, the substrate 100 may be further prepared by placing the substrate 100 into a sodium hydroxide (NaOH) solution to expose the silanols on the glass to allow for proper bonding of the volatile compound sorptive coating mixture. The glass substrate may then be rinsed using deionized water. If, for example, a metal substrate is used, a metal surface preparation may be completed. See A. Franquet, H. Terryn and J. Vereecken. Surf. Interface Anal., 36: 681-684 (2004). The metal substrate may be prepared by immersing the substrate in a mixture of an approximately 1 to 5 ratio of perchloric acid to ethanol at a temperature of approximately 10° C. The metal substrate is then ultrasonically cleaned by dipping it successively into hexane, acetone, and methanol. The metal substrate is held in each chemical for approximately 5 minutes. An alkaline cleaning may then be performed by immersing the ultrasonically clean substrate for approximately 8 minutes, at a temperature of approximately 65° C., in a 7.5 vol. % AC1055 (Chemetall, Frankfurt, Germany) solution using distilled water as a solvent. The metal substrate are then thoroughly rinsed with distilled water and blow-dried.

A volatile compound sorptive coating mixture may be prepared or obtained. If, for example, the desired volatile compound sorptive coating 108 is poly(dimethylsiloxane) (PDMS), a coating mixture that includes chlorine terminated poly(dimethylsiloxane) and dichloromethane may be prepared. Preferably, the coating mixture includes an approximately 3 to 1 ratio of chlorine terminated poly(dimethylsiloxane) to dichloromethane. Any other volatile compound sorptive coating mixture that is suitable for absorption and/or adsorption of a target vapor from a volatile compound such as an explosive, a taggant in an explosive, a controlled substance, a biohazard, or mixtures thereof may be used.

The volatile compound sorptive coating mixture may also be prepared using, for example, a sol-gel technique. The sol-gel process involves the transition of a system from a liquid "sol" to a solid "gel" phase. In this process, the precursor, MTMOS, for example, is subject to hydrolysis and polycondensation to form a colloidal suspension ("sol"). If, for example, a PDMS coating is desired, a PDMS coating mixture may be prepared by sol-gel technique. The sol-gel preparation of a PDMS coating mixture may include, for example, dissolving vinyl terminated PDMS in $MeCl_2$, adding MTMOS, PMHS, and TFA.

The substrate 100 is coated with the volatile compound sorptive coating mixture to form a volatile compound sorptive coating 108. The substrate 100 may be coated by, spin coating or dip coating, for example. If the substrate 100 is glass, the substrate 100 may be coated, for example, with PDMS using an oxygen-plasma treatment. Any other suitable coating method may be used as well. To coat the substrate 100 by dip coating, for example, the substrate 100 is immersed in the volatile compound sorptive coating mixture and held for a period of time. The substrate 100 is then withdrawn from the volatile compound sorptive coating mixture and the solvent is allowed to evaporate. To coat the substrate 100 using a spin coating method, for example, the volatile compound sorptive coating mixture is deposited on the substrate 100. The substrate 100 is then rotated at high speeds to distribute the volatile compound sorptive coating mixture by centrifugal force. Rotation is continued until the desired thickness of a volatile compound sorptive coating 108 is achieved. The coating process may further include curing the coated substrate 100. The coated substrate 100 may be cured, for example, in an oven under nitrogen.

The volatile compound sorptive coating 108 disposed on the substrate 100 is capable of absorbing and/or adsorbing a target vapor from a volatile compound such as an explosive, a taggant in an explosive, a controlled substance, a biohazard, or mixtures thereof. Preferably, the volatile compound sorptive coating 108 is PDMS or sol-gel PDMS. Any volatile compound sorptive coating 108 suitable for absorptive and/or adsorptive of target vapors from a volatile compound such as an explosive, a taggant in an explosive, a controlled substance, a biohazard, or mixtures thereof may be used. Other suitable volatile compound sorptive coatings 108 may include, for example, carbowax, carboxan, divinylbenzene (DVB), polyurethane, and polyacrylate. Mixed phase volatile compound sorptive coatings 108 may also be used and may include, for example, carbowax/polyethylene glycol (CW/PEG), carbowax/templated resin (CW/TPR), carboxen/polydimethylsiloxane (CAR/PDMS), divinylbenzene/carboxen/polydimethylsiloxane (DVB/CAR/PDMS), polydimethylsiloxane/divinylbenzene (PDMS/DVB).

The SPME device 106 may be used for sorption of any vapor capable of being sorbed and concentrated therein or thereon, preferably, a target vapor from a volatile compound such as an explosive, a taggant in an explosive, a controlled substance, a biohazard, or mixtures thereof by absorption and/or adsorption of the vapor by the volatile compound sorptive coating 108. To extract a target vapor from a volatile compound, the SPME device 106 may be first exposed to air or another gaseous atmosphere in an enclosed space containing an object to allow for absorption and/or adsorption of one or more target vapors and concentration of the target vapor in and/or on the SPME device 106. Alternatively, a test object may be contacted with a volume of gas and the SPME device 106 may be exposed to the volume of gas to allow for absorption and/or adsorption of vapors contained in the volume of gas. The SPME device 106 may then be introduced into a sample receiving area 112 of an IMS 110 for volatilization of the target vapor from the SPME device 106 and introduction of the target vapor into the IMS 110. The IMS 110 can then detect and characterize the vapor. Thermal desorption may be used, for example, to introduce the vapor into the IMS 110.

The combination of SPME and IMS can have a large range of applications; all that is required is extraction of the target vapor by the SPME-phase and the ability to detect the vapor by IMS. As described, the application of the SPME-INS interface 10, the new and improved SPME device 106, and the method of extraction, detection, and characterization will allow for the vapor sampling of volatile compounds such as explosives, taggants in explosives, controlled substance, biohazards, or mixtures thereof and detection and characterization of the vapor samples by IMS. The combination of SPME and IMS using the new and improved SPME devices 106 may allow for more accurate detection and characterization and may, also, simplify the detection process, and allow for rapid field sampling of large rooms and containers.

Moreover, because the SPME device 106 has increased amount of SPME-phase able to participate in extraction it can absorb and/or adsorb an increased amount of the target vapor and thereby improve sensitivity and accuracy of the detection method without appreciably increasing the extraction time. The improved sensitivity may allow for detection and characterization of characteristic vapors that cannot be detected by prior art methods or devices.

The present invention has been described with reference to specific examples, which are intended to be illustrative only and not to be limiting of the invention. It will be apparent to those of ordinary skill in the art that changes, additions, and/or deletions may be made to the disclosed embodiments without departing from the spirit and scope of the invention.

What is claimed:

1. A system for solid phase microextraction (SPME) and ion mobility spectrometry detection, comprising:
    an ion mobility spectrometer (IMS) having a sample receiving area comprising a device receiving region defined by a circular circumference within which a planar, circular, disc shaped device can reside; and
    a SPME device residing in the device receiving region for detection and characterization of a sorbed vapor, the SPME device comprising:
    a substrate having first and second opposed surfaces and one or more side surfaces integrally connected to the first and second surfaces, the first and second surfaces being circular and planar surfaces;
    a volatile compound sorptive coating disposed on the first surface and the second surface, wherein the volatile compound sorptive coating is exposed and capable of sorbing a vapor from a material selected from the group consisting of an explosive, a taggant in an explosive, a controlled substance, a biohazard, or mixtures thereof;
    wherein the SPME device has a thickness, as measured from the distance between the first and second surfaces, of about 0.5 mm to about 2 mm; and
    wherein a total surface area of the surfaces coated with the volatile compound sorptive coating is at least 25 mm$^2$; and
    wherein the SPME device resides in the device receiving region of the sample receiving area of the IMS such that the first and second surfaces are concentric with the device receiving region and the side surfaces are in contact with the circumference of the device receiving region.

2. The system of claim 1, wherein the SPME device has a flat disc shape.

3. The system of claim 1, wherein the volatile compound sorptive coating is polydimethyl siloxane (PDMS).

4. The SPME device of claim 1, wherein one or more of the first and second surfaces are planar and has a surface area of at least 5 mm$^2$.

5. The SPME device of claim 1, wherein the volatile compound sorptive coating is disposed on the first and second surfaces and the one or more side surfaces.

6. The SPME device of claim 1, wherein the total surface area of the surfaces coated with the volatile compound sorptive coating is from approximately 500 to 1000 mm$^2$.

7. A system for solid phase microextraction (SPME) and ion mobility spectrometry detection, comprising:
    an ion mobility spectrometer (IMS) having a sample receiving area comprising a circular device receiving region; and
    a SPME device residing in the device receiving region for detection and characterization of a sorbed vapor, the SPME device comprising:
    a substrate having opposed surfaces, the surfaces each being circular and planar; and
    a volatile compound sorptive coating disposed on the substrate so as to form a continuous coating covering the entirety of each of the opposed surfaces, said coating capable of sorbing a vapor from a material selected from the group consisting of an explosive, a taggant in an explosive, a controlled substance, a biohazard, and mixtures thereof,
    wherein the SPME device has a thickness, as measured from the distance between the opposed surfaces, of about 0.5 mm to about 2 mm
    wherein the SPME device has a coating surface area of at least 25 mm$^2$; and
    wherein the SPME device resides in the device receiving region of the sample receiving area of the IMS such that the opposed surfaces of the SPME device are concentric with the device receiving region.

8. The system of claim 7, wherein the substrate is glass.

9. The system of claim 7, wherein the substrate is metal.

10. The system of claim 7, wherein the SPME device has a coating surface area of from approximately 500 to 1000 mm$^2$.

* * * * *